(12) United States Patent
Liu et al.

(10) Patent No.: US 8,367,674 B2
(45) Date of Patent: Feb. 5, 2013

(54) PIPERAZINE DERIVATIVES

(75) Inventors: Julie F. Liu, Lexington, MA (US); Rose Persichetti, Stow, MA (US)

(73) Assignee: CoNCERT Pharmaceuticals, Inc., Lexington, MA (US)

(*) Notice: Subject to any disclaimer, the term of this patent is extended or adjusted under 35 U.S.C. 154(b) by 482 days.

(21) Appl. No.: 12/386,492

(22) Filed: Apr. 17, 2009

(65) Prior Publication Data

US 2009/0270336 A1    Oct. 29, 2009

Related U.S. Application Data

(60) Provisional application No. 61/124,665, filed on Apr. 17, 2008, provisional application No. 61/127,906, filed on May 16, 2008.

(51) Int. Cl.
*C07D 401/14* (2006.01)
*A61K 31/506* (2006.01)

(52) U.S. Cl. .................. 514/252.18; 544/295
(58) Field of Classification Search .......... 544/295; 514/252.18
See application file for complete search history.

(56) References Cited

U.S. PATENT DOCUMENTS

| | | | |
|---|---|---|---|
| 6,221,335 | B1 | 4/2001 | Foster |
| 6,391,865 | B1 | 5/2002 | Baroudy et al. |
| 6,440,710 | B1 | 8/2002 | Keinan et al. |
| 6,603,008 | B1 | 8/2003 | Ando et al. |
| 6,689,765 | B2 | 2/2004 | Baroudy et al. |
| 7,517,990 | B2 | 4/2009 | Ito et al. |
| 2003/0069252 | A1 | 4/2003 | Baroudy et al. |
| 2007/0082929 | A1 | 4/2007 | Gant et al. |
| 2007/0197533 | A1* | 8/2007 | Zhou et al. .............. 514/241 |
| 2007/0197695 | A1 | 8/2007 | Potyen et al. |
| 2008/0103122 | A1 | 5/2008 | Veltri |
| 2010/0120786 | A1 | 5/2010 | Liu et al. |

FOREIGN PATENT DOCUMENTS

| | | |
|---|---|---|
| EP | 1 870 420 A1 | 12/2007 |
| WO | WO 95/26325 A2 | 10/1995 |
| WO | WO 00/66551 | 11/2000 |
| WO | WO 00/66558 | 11/2000 |
| WO | WO 03/084950 A1 | 10/2003 |
| WO | WO 2005/016226 A2 | 2/2005 |
| WO | WO 2006/074264 A2 | 7/2006 |
| WO | WO 2007/118651 A1 | 10/2007 |
| WO | WO 2009/128947 A1 | 10/2009 |

OTHER PUBLICATIONS

Marcus et al., PubMed Abstract (Intervirology 45(4-6):260-6), 2002.* van Heeswijk et al., PubMed Abstract (Antivir Ther. 6(4):201-29) Dec. 2001.*

Havlioglu et al., Slit proteins, potential endogenous modulators of inflammation, Journal of NeuroVirology, 8, pp. 486-495, 2002.*

Ghosal, A., et al., "Identification of Human Liver Cytochrome P450 Enzymes Involved in Biotransformation of Vicriviroc, a CCR5 Receptor Antagonist," *Drug Metabolism and Disposition*, 35(12): 2186-2195 (2007).

Notification of Transmittal of the International Search Report and the Written Opinion of the International Searching Authority, or the Declaration, International Application No. PCT/US2009/002424, Date of Mailing Oct. 6, 2009.

Fisher, M.B. et al., "The Complexities Inherent in Attempts to Decrease Drug Clearance by Blocking Sites of CYP-Mediated Metabolism," *Curr. Opin. Drug Discov. Devel.*, 9(1):101-109 (2006).

Kushner, D.J. et al., "Pharmacological Uses and Perspectives of Heavy Water and Deuterated Compounds," *Can. J. Physiol. Pharmacol.*, 77:79-88 (1999).

McCombie, SW et al., "Piperazine-based CCR5 Antagonists as HIV-1 Inhibitors. III: Synthesis, Antiviral and Pharmacokinetic Profiles of Symmetrical Heteroaryl Carboxamides," *Bioorg Med Chem Lett* 13:567-571 (2003).

Revill, P. et al., "Vicriviroc," *Drugs Fut* 32(5):417-427 (2007).

Tagat, JR et al., "Piperazine-based CCR5 Antagonists as HIV-1 Inhibitors. II. Discovery of 1-[(2,4-Dimethyl-3-pyridinyl)carbonyl]-4-methyl-4-[3(S)-methyl-4-[1(S)-[4-(trifluoromethyl)phenyl]ethyl]-1-piperazinyl]-piperidine N1-Oxide (Sch-350634), an Orally Bioavailable, Potent CCR5 Antagonist," *J Med Chem* 44(21):3343-3346 (2001).

Tagat, JR et al., "Piperazine-based CCR5 Antagonists as HIV-1 Inhibitors. IV. Discovery of 1-[(4,6-Dimethyl-5-pyrimidinyl)carbonyl]-4-[4-{2-methoxy-1(R)-4-(trifluoromethyl)phenyl}ethyl-3(S)-methyl-1-piperazinyl]-4-methylpiperidine (Sch-417690/Sch-D), a Potent, Highly Selective, and Orally Bioavailable CCR5 Antagonist," *J Med Chem* 47(10):2405-2408 (2004).

Baille, T. A., "The Use of Stable Isotopes in Pharmacological Research," *Pharmacological Reviews*, 33(2): 81-132 (1981).

Browne, T. R., "Stable Isotope Techniques in Early Drug Development: An Economic Evaluation," *J. Clin. Pharmacol.*, 38: 213-220 (1998).

Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).

Dyck, L. E., et al., "Effects of Deuterium Substitution on the Catabolism of β-Phenylethylamine: An in Vivo Study," *Journal of Neurochemistry*, 46(2): 399-404 (1986). Foster, A. B., "Deuterium Isotope Effects in Studies of Drug Metabolism," *Trends in Pharmacological Sciences*, 5: 524-527 (1984).

Foster, A. B., "Deuterium Isotope Effects in the Metabolism of Drugs and Xenobiotics: Implications for Drug Design," *Advances in Drug Research*, 14: 1-40 (1985).

Gouyette, A., "Synthesis of Deuterium-labelled Elliptinium and its Use in Metabolic Studies," *Biomedical and Environmental Mass Spectrometry*, 15: 243-247 (1988).

Haskins, N. J., "The Application of Stable Isotopes in Biomedical Research," *Biomedical Mass Spectrometry*, 9(7): 269-277 (1982).

Honma S., et al., "The Metabolism of Roxatidine Acetate Hydrochloride," *Drug Metabolism and Disposition*, 15(4): 551-559 (1987).

(Continued)

*Primary Examiner* — Deepak Rao
(74) *Attorney, Agent, or Firm* — Hamilton, Brook, Smith & Reynolds, P.C.

(57) ABSTRACT

This invention relates to novel compounds that are piperazine derivatives, and pharmaceutically acceptable salts thereof. More specifically, the invention relates to novel piperazine compounds that are derivatives of the chemokine CCR5 receptor antagonist, vicriviroc. This invention also provides pyrogen-free compositions comprising one or more compounds of the invention and a carrier and the use of the disclosed compounds and compositions in methods of treating diseases and conditions that are treated by administering chemokine CCR5 receptor antagonists, such as vicriviroc. The invention also relates to the use of one or more of the disclosed compounds as reagents in analytical studies involving vicriviroc.

10 Claims, 1 Drawing Sheet

OTHER PUBLICATIONS

Pieniaszek, H. J., et al., "Moricizine Bioavailability via Simultaneous, Dual, Stable Isotope Administration: Bioequivalence Implications," *J. Clin. Pharmacol*, 39: 817-825 (1999).

Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).

Wolen, R. L., "The Application of Stable Isotopes to Studies of Drug Bioavailability and Bioequivalence," *J. Clin. Pharmacol.*, 26: 419-424 (1986).

Notification Concerning Transmittal of International Preliminary Report on Patentability for PCT/US2009/002424, mailed Oct. 28, 2010.

Office Action for U.S. Appl. No. 12/603,380; Date Mailed: Aug. 4, 2011.

Pharmacokinetic Data in Chimpanzees for Compounds 101 and 105 of the Invention and Vicriviroc. ( Date: Sep. 24, 2009).

* cited by examiner

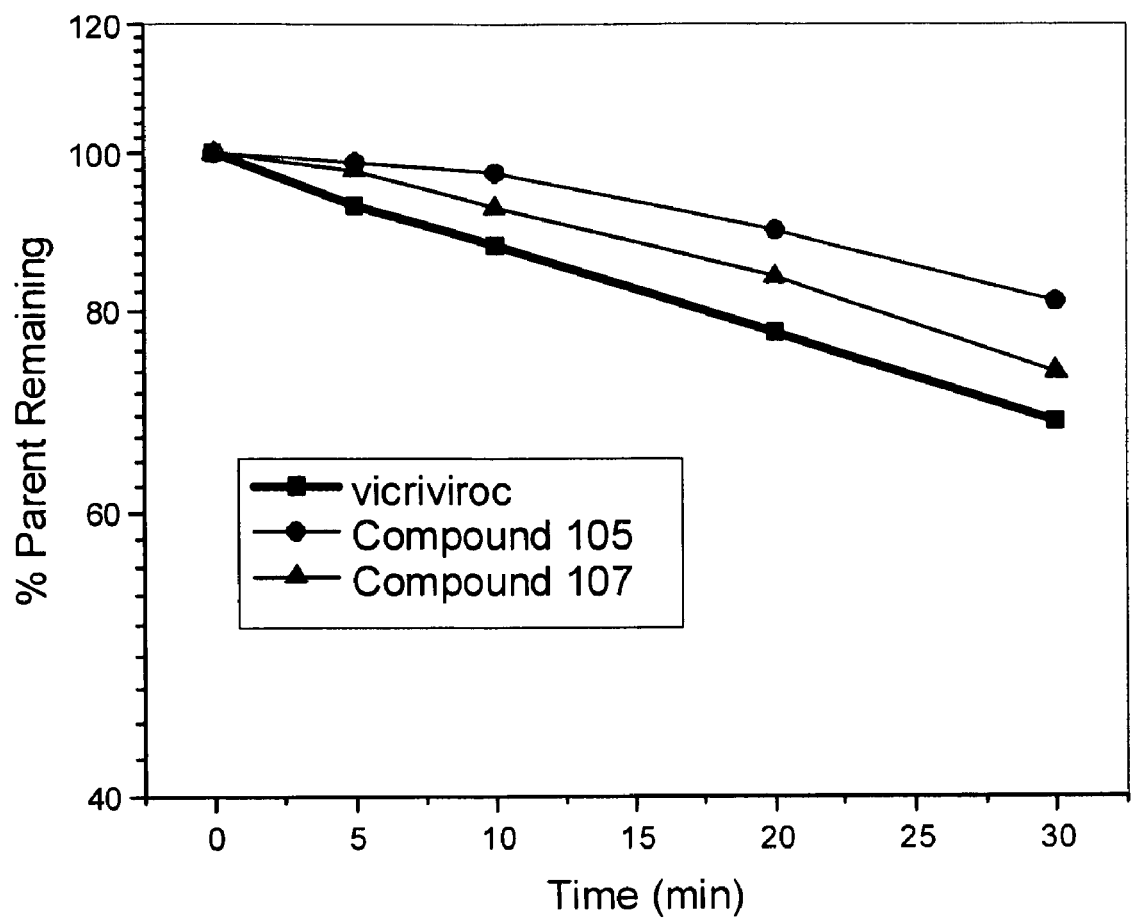

PIPERAZINE DERIVATIVES

RELATED APPLICATIONS

This application claims the benefit of U.S. Provisional Application No. 61/124,665, filed on Apr. 17, 2008 and U.S. Provisional Application No. 61/127,906, filed on May 16, 2008. The entire teachings of the above applications are incorporated herein by reference.

BACKGROUND OF THE INVENTION

Vicriviroc, also known as 5-[4-[4-[2-methoxy-1(R)-[4-(trifluoromethyl)phenyl]ethyl]-3(S)-methylpiperazin-1-yl]-4-methylpiperidin-1-ylcarbonyl]-4,6-dimethylpyrimidine, blocks the entry of the HIV virion into the host cell through its action as a chemokine CCR5 receptor antagonist.

Vicriviroc is currently in phase II clinical trials for HIV infection. It has been described as safe, well-tolerated and without QTc effects associated with cardiovascular events.

Despite the beneficial activities of vicriviroc, there is a continuing need for new compounds to treat HIV infection.

SUMMARY OF THE INVENTION

This invention relates to novel compounds that are piperazine derivatives, and pharmaceutically acceptable salts thereof. More specifically, the invention relates to novel piperazine compounds that are derivatives of the chemokine CCR5 receptor antagonist, vicriviroc. This invention also provides pyrogen-free compositions comprising one or more compounds of the invention and a carrier and the use of the disclosed compounds and compositions in methods of treating diseases and conditions that are treated by administering chemokine CCR5 receptor antagonists, such as vicriviroc.

BRIEF DESCRIPTION OF THE DRAWINGS

The FIGURE depicts the stability of certain compounds of the invention in human liver microsomes as compared to vicriviroc.

DETAILED DESCRIPTION OF THE INVENTION

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of vicriviroc will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Gannes L Z et al., Comp Biochem Physiol Mol Integr Physiol 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts, solvates or hydrates of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The disclosed compounds may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms.

When the stereochemistry of the disclosed compounds is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% optically pure. Percent optical purity by weight is the ratio of the weight of the enantiomer over the weight of the enantiomer plus the weight of its optical isomer.

When a disclosed compound is named or depicted by structure without indicating the stereochemistry, and has at least one chiral center, it is to be understood that the name or structure encompasses one enantiomer of the compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

"Tert", "ᵗ", and "t-" each refer to tertiary.

"US" refers to the United States of America.

"FDA" refers to Food and Drug Administration.

"NDA" refers to New Drug Application.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula (I):

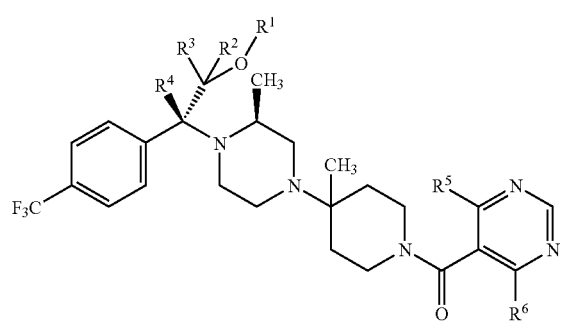

(I)

or a pharmaceutically acceptable salt thereof, wherein:

each of $R^1$, $R^5$ and $R^6$ is selected from —$CH_3$, —$CH_2D$, —$CHD_2$ and —$CD_3$;

each of $R^2$, $R^3$ and $R^4$ is independently selected from H or D; and at least one R variable comprises a deuterium atom.

The present invention also provides a compound of Formula (IA):

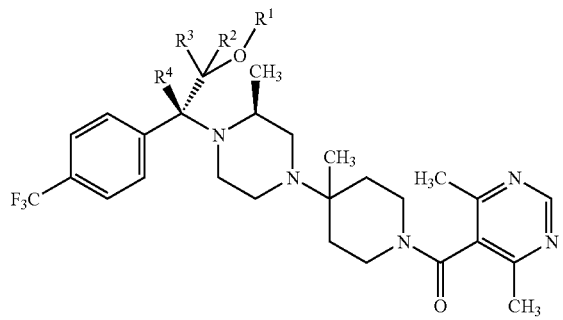

(IA)

or a pharmaceutically acceptable salt thereof, wherein:
R¹ is selected from —CH₃, —CH₂D, —CHD₂ and —CD₃;
each of R², R³ and R⁴ is independently selected from H or D; and
at least one R variable comprises a deuterium atom.

In other embodiments of Formula I, IA or both:
a) R¹ is selected from —CH₃ and —CD₃;
b) R⁵ is selected from —CH₃ and —CD₃;
c) R⁶ is selected from —CH₃ and —CD₃;
d) R⁵ and R⁶ are the same; and
e) R² and R³ are the same.

In a more specific embodiment, a compound of Formula IA has the features set forth in at least two of a) through e), above. Exemplary combinations include, but are not limited to: b+a; c+a; e+a; e+b; e+c; d+a; d+b; d+c; d+e; c+b+a; e+b+a; e+c+a; d+b+a; d+c+a; d+e+a; d+e+b; d+e+c; e+c+b+a; d+c+b+a; d+e+b+a; and d+e+c+a;

In still another embodiment of Formula I, R² and R³ are deuterium, the compound having the structure depicted in Formula IB:

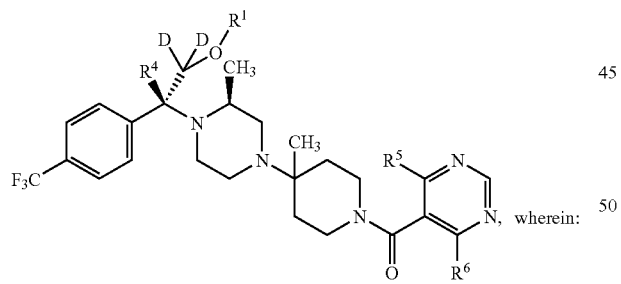

(IB), wherein:

R¹ is selected from —CH₃ and —CD₃;
R⁴ is selected from hydrogen and deuterium; and
each of R⁵ and R⁶ is independently selected from —CH₃ and —CD₃.

In one embodiment of Formula IB, R¹ is CD₃. In one aspect of this embodiment, R⁴ is hydrogen and R⁵ and R⁶ are —CD₃. In an alternate aspect, R⁴ is hydrogen, and R⁵ and R⁶ are —CH₃.

In another embodiment of Formula IB, R⁴ is hydrogen and each of R¹, R⁵ and R⁶ are —CH₃.

In still another embodiment of Formula I, each of R¹, R⁵ and R⁶ are —CD₃, the compound having the structure depicted in Formula IC:

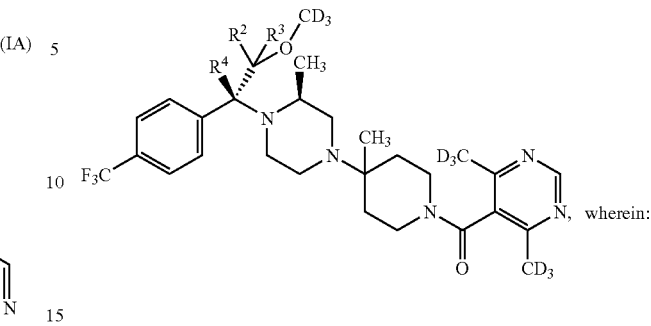

(IC), wherein:

each of R², R³ and R⁴ is independently selected from hydrogen and deuterium. In one aspect of this embodiment, each of R² and R³ is hydrogen. In an alternate aspect of this embodiment, each of R² and R³ is deuterium.

In yet another embodiment, the compound is selected from any one of the compounds set forth below.

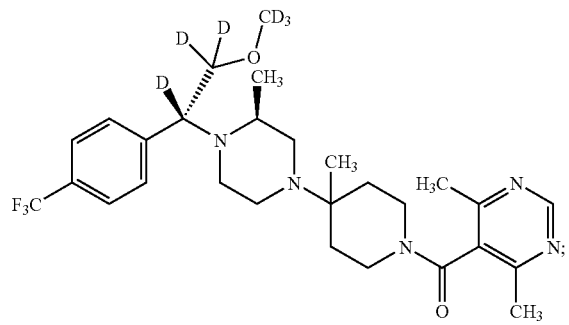

Compound 100

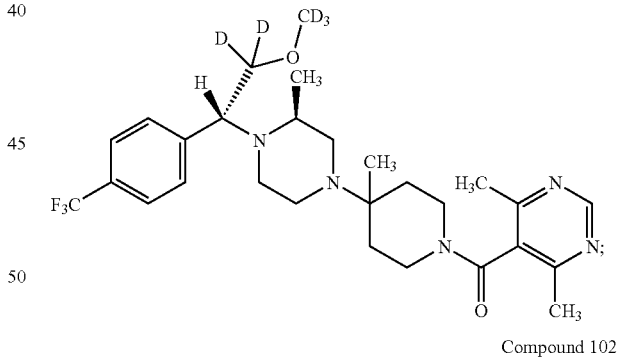

Compound 101

Compound 102

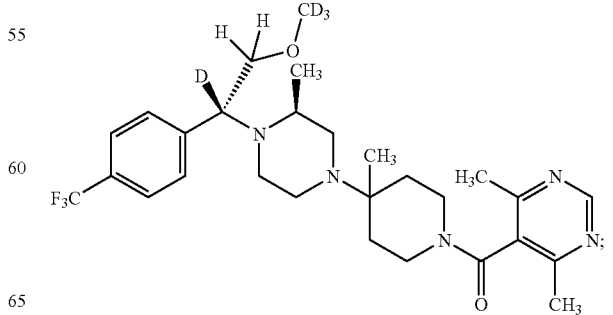

Compound 103

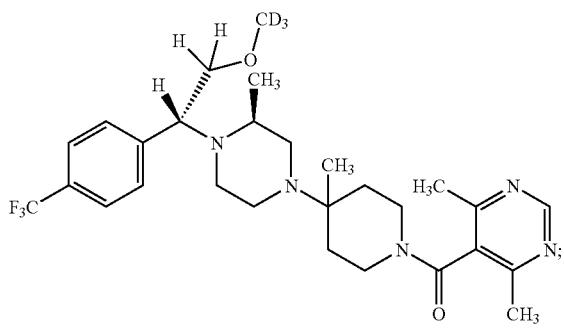

Compound 106

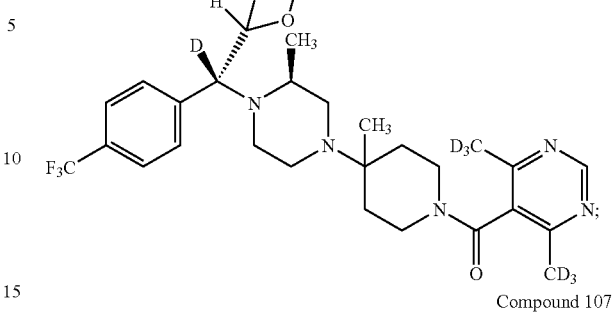

Compound 107

Compound 108

Compound 104

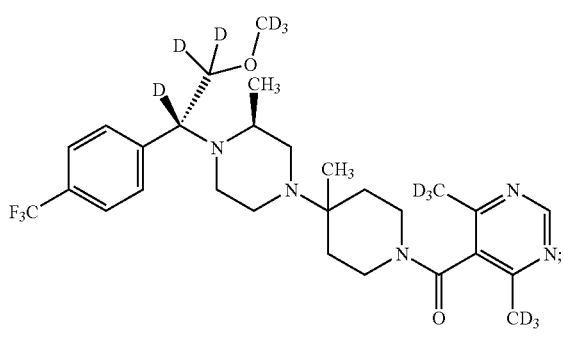

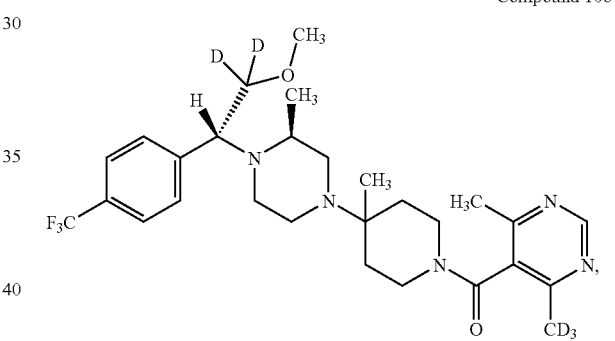

Compound 105

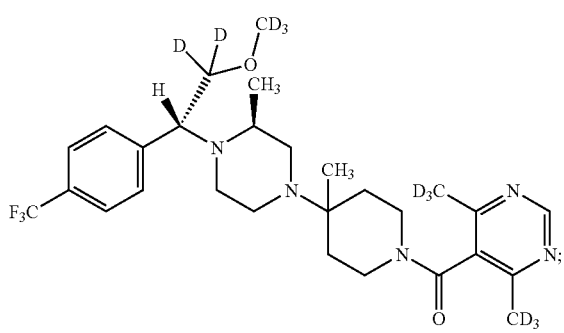

a pharmaceutically acceptable salt of any of the foregoing.

In another set of embodiments, any atom not designated as deuterium in any of the embodiments set forth above is present at its natural isotopic abundance.

The synthesis of compounds of Formulas (I), (IA), (IB) or (IC) can be readily achieved by synthetic chemists of ordinary skill. Relevant procedures and intermediates are disclosed, for instance in U.S. Pat. Nos. 6,689,765 and 6,391,865, and in PCT publications WO2000066551, WO2003084950, and WO 2006074264, and in the following literature articles: Tagat, J R et al., J Med Chem, 2004, 47(10): 2405-2408; and Revill, P et al., Drugs Fut, 2007, 32(5): 417; and Tagat, J R et al., J Med Chem, 2001, 44(21): 3343-3346; and McCombie, S W et al., Bioorg. Med. Chem. Lett., 2003, 13: 567-571.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

Exemplary Synthesis

A convenient method for synthesizing compounds of Formula (I) is depicted in Scheme 1.

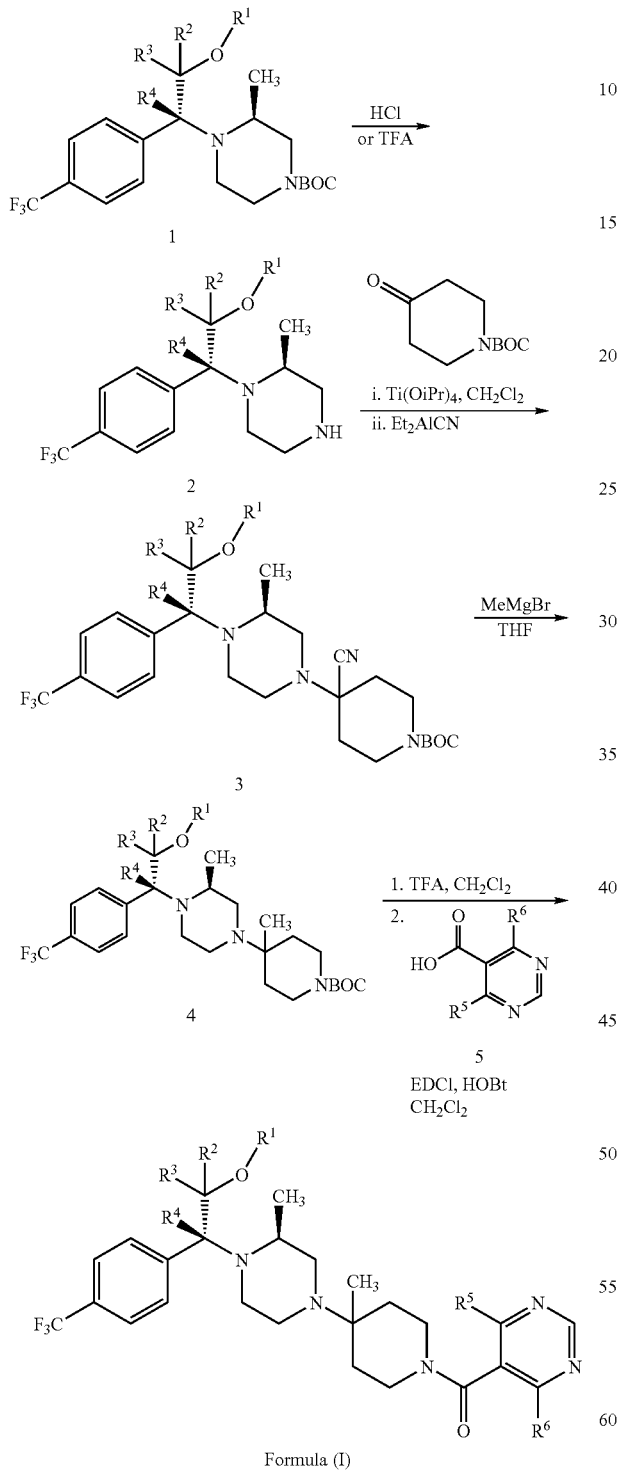

Scheme 1 provides a route for preparing compounds of Formula (I) which follows the general methods of US 20060105964(A1). BOC-protected amine 1 may be deprotected via treatment with either HCl or trifluoroacetic acid to afford amine 2. Treatment of amine 2 with commercially-available N-(tert-butoxycarbonyl)-4-piperidone and titanium isopropoxide, followed by treatment with diethylaluminum cyanide, affords nitrile 3. Treatment with methylmagnesium bromide provides intermediate 4. The BOC protecting group may be cleaved with trifluoroacetic acid and the resulting amine may be coupled with appropriately-deuterated carboxylic acid 5 in the presence of EDCI and HOBt to afford compounds of Formula (I).

Convenient methods for preparing appropriately-deuterated versions of amine I are depicted in Schemes 2 and 3.

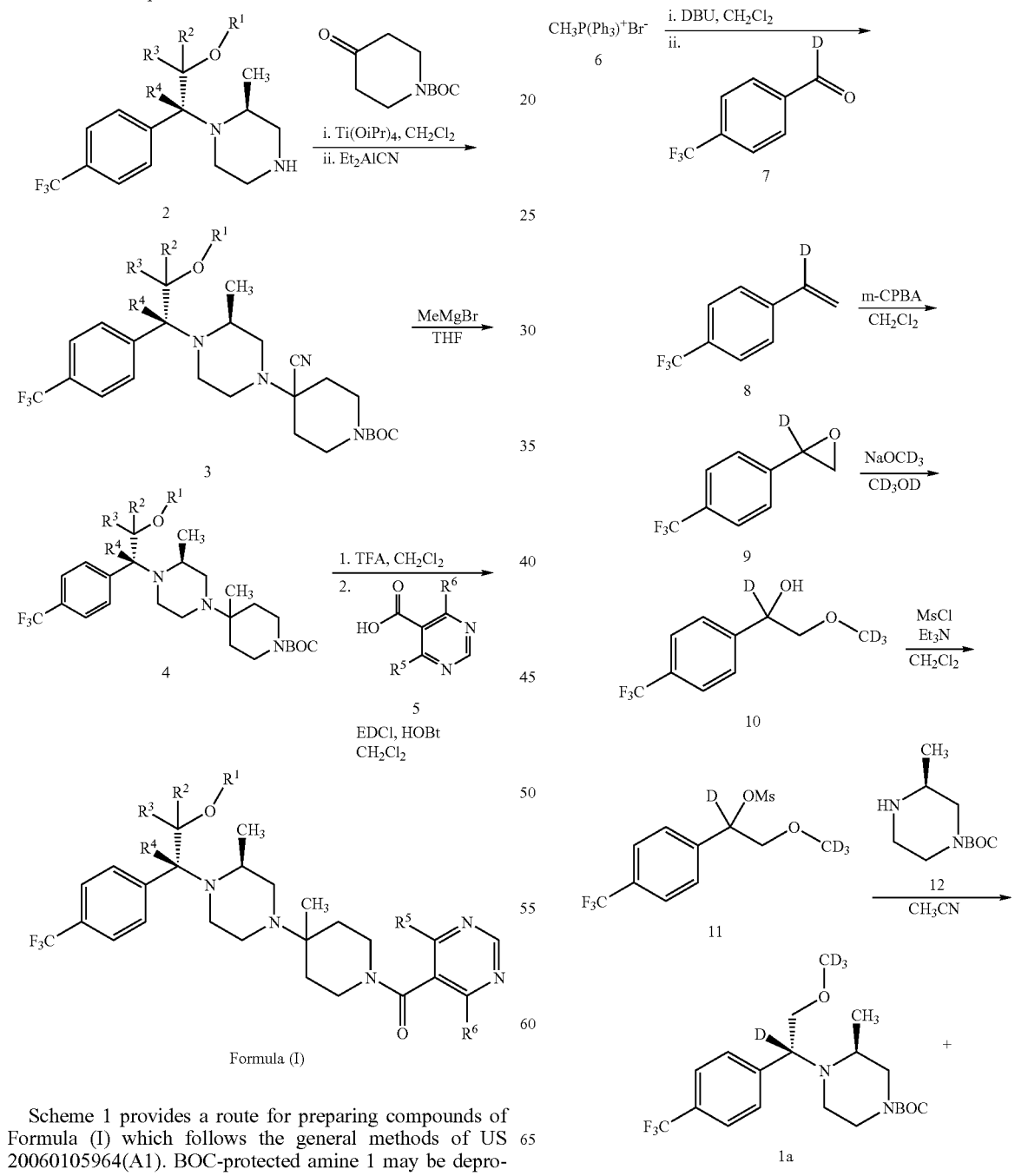

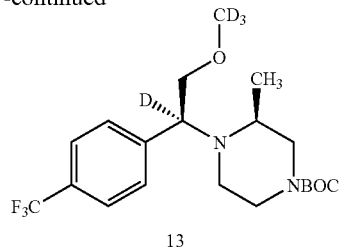

13

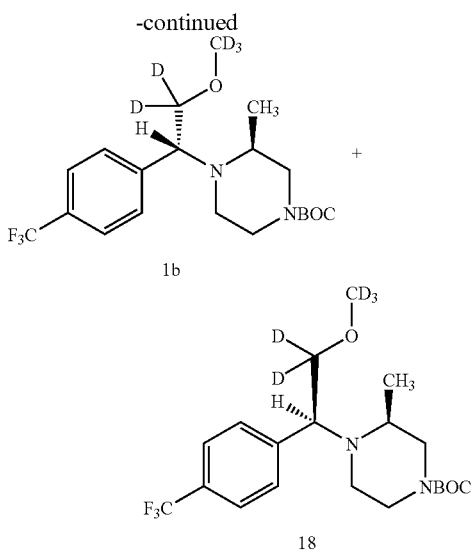

1b

18

Scheme 2 provides a route for preparing an appropriately-deuterated version of amine 1 wherein $R^1$ is $CD_3$, each of $R^2$ and $R^3$ are hydrogen, and $R^4$ is deuterium. Treatment of commercially-available methyltriphenylphosphonium bromide with DBU, followed by commercially available deuterated aldehyde 7 (98 atom % D) provides deuterated styrene derivative 8 according to the general methods of Okuma, K et al., Bulletin of the Chemical Society of Japan, 2003, 76(8): 1675-1676. According to the methods of US 20060105964(A1), treatment of styrene derivative 8 with mCPBA in dichloromethane provides the epoxide 9, which then may be treated with deuterated sodium methoxide in deuterated methanol (>99 atom % D) to yield the benzyl alcohol 10. The reaction of 10 with methanesulfonyl chloride and $Et_3N$ affords the mesylate 11, which then may be condensed with commercially-available (S)-1-BOC-3-methylpiperazine 12 in acetonitrile to provide a diastereomeric mixture of compounds 1a and 13, which are separable via flash chromatography.

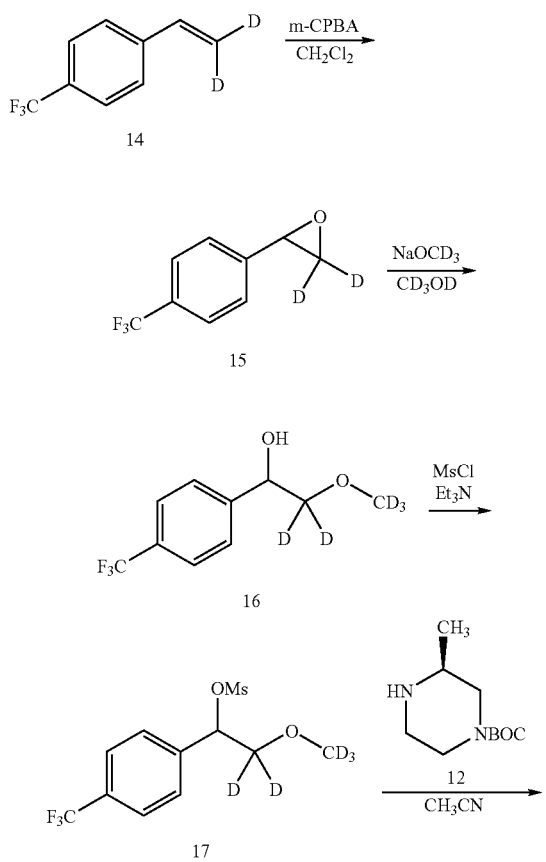

Scheme 3 provides a route for preparing an appropriately-deuterated version of amine 1 wherein $R^1$ is $CD_3$, $R^2$ and $R^3$ are each deuterium and $R^4$ is hydrogen. According to the methods of US 20060105964(A 1), treatment of known deuterated styrene derivative 14 (Casalnuovo, A; et al. JACS (1994), 116(22), 9869-82 [reported to be 89-91% $d_2$, and 9-10% $d_1$) with mCPBA in dichloromethane provides the epoxide 15, which then may be treated with deuterated sodium methoxide in deuterated methanol to yield the benzyl alcohol 16. The reaction of 16 with methanesulfonyl chloride and $Et_3N$ affords the mesylate 17, which then may be condensed with commercially-available (S)-1-BOC-3-methylpiperazine 12 in acetonitrile to provide a diastereomeric mixture of compounds 1b and 18, which are separable by flash chromatography.

It will be appreciated by one skilled in the art that Schemes 2 and 3 can be readily modified to provide intermediates 1 which lead to other compounds of Formula (I) having various combinations of R variables.

A convenient method for preparing an appropriately-deuterated carboxylic acid 5 is depicted in Scheme 4.

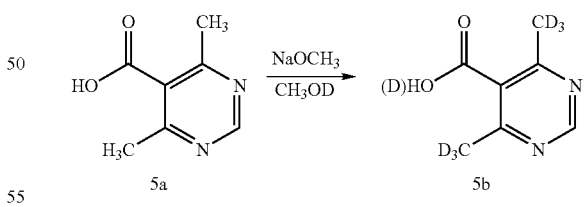

Scheme 4 provides a route for preparing an appropriately-deuterated carboxylic acid 5 wherein $R^5$ and $R^6$ are both $CD_3$. Commercially-available 4,6-dimethylpyrimidine-5-carboxylic acid 5a may be treated with $NaOCH_3$ in $CH_3OD$ (99.5 atom % D) to afford deuterated carboxylic acid 5b.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds of Formulas (I), (IA), (IB) or (IC) and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3rd Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formulas (I), (IA), (IB) or (IC) (e.g., including any of the formulae herein), or a pharmaceutically acceptable salt; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as vicriviroc. Such agents include those indicated as being useful in combination with vicriviroc including, but not limited to, those described in WO 2002056902 and WO 2006060175.

Preferably, the second therapeutic agent is an agent useful in the treatment or prevention of a disease or condition selected from HIV, solid organ transplant rejection, graft vs. host disease, arthritis, inflammatory bowel disease, atopic dermatitis, psoriasis, asthma, allergies, multiple sclerosis and hepatitis C.

In one embodiment, the second therapeutic agent is selected from other anti-retroviral agents including, but not limited to, an HIV protease inhibitor (e.g., amprenavir, fosamprenavir, tipranavir, indinavir, saquinavir, lopinavir, ritonavir, darunavir, or nelfinavir), a non-nucleoside reverse transcriptase inhibitor ("NNRTI") (e.g., etravirine, delavirdine, efavirenz, nevirapine, or rilpivirine), a nucleoside/nucleotide reverse transcriptase inhibitor ("NRTI") (e.g., zidovudine, lamivudine, emtricitabine, zidovudine, tenofovir disoproxil fumarate, didanosine, stavudine, abacavir, racivir, amdoxovir, apricitabine, or elvucitabine), a second viral entry inhibitor (e.g., enfuvirtide, maraviroc, PRO 140, or TNX-355), an integrase inhibitor (e.g., raltegravir, or elvitegravir), an immune based antiretroviral agent (e.g., immunitin, proleukin, remune, BAY 50-4798 or IR103), a viral maturation inhibitor (e.g., bevirimat), a cellular inhibitor (e.g., droxia or hydroxurea), or combinations of two or more of the above.

In one embodiment, the second therapeutic agent is selected from emtricitabine, tenofovir disoproxil fumarate, ritonavir, lamivudine, zidovudine, tipranavir, enfuvirtide and ancriviroc.

In a more specific embodiment, the second therapeutic agent is selected from ritonavir, lamivudine, emtricitabine, tenofovir disoproxil fumarate. and zidovudine.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, an effective amount can be an amount which is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.05 to 1500 mg per treatment. In more specific embodiments the dose can range from about 0.5 to 750 mg, or from about 1 to 300 mg, or most specifically from 5 to 150 mg per treatment. Treatment typically is administered once per day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for vicriviroc.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting or reducing the activity of the chemokine CCR5 receptor in a cell, comprising contacting a cell with one or more compounds of Formulas (I), (IA), (IB) or (IC) herein.

According to another embodiment, the invention provides a method of treating a disease in a patient in need thereof that is beneficially treated by a chemokine CCR5 receptor antagonist, such as vicriviroc, comprising the step of administering to said patient an effective amount of a compound or a composition of this invention. Such diseases are well known in the art and are disclosed in, but not limited to, the following patents and published applications: US 2003069252; and WO 2005016226. Such diseases include, but are not limited to, HIV, solid organ transplant rejection, graft vs. host disease, arthritis, inflammatory bowel disease, atopic dermatitis, psoriasis, asthma, allergies, multiple sclerosis and hepatitis C.

In one particular embodiment, the method of this invention is used to treat HIV infection in a patient in need thereof.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with vicriviroc. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In one embodiment, the patient is suffering from an HIV infection and the second therapeutic agent is selected from one or more of an HIV protease inhibitor (e.g., amprenavir, fosamprenavir, tipranavir, indinavir, saquinavir, lopinavir, ritonavir, darunavir, or nelfinavir), a non-nucleoside reverse transcriptase inhibitor ("NNRTI") (e.g., etravirine, delavirdine, efavirenz, nevirapine, or rilpivirine), a nucleoside/nucleotide reverse transcriptase inhibitor ("NRTI") (e.g., zidovudine, lamivudine, emtricitabine, zidovudine, tenofovir disoproxil fumarate, didanosine, stavudine, abacavir, racivir, amdoxovir, apricitabine, or elvucitabine), a second viral entry inhibitor (e.g., enfuvirtide, maraviroc, PRO 140, or TNX-355), an integrase inhibitor (e.g., raltegravir, or elvitegravir), an immune based antiretroviral agent (e.g., immunitin, proleukin, remune, BAY 50-4798 or IR103), and a viral maturation inhibitor (e.g., bevirimat), a cellular inhibitor (e.g., droxia or hydroxyurea).

In a more specific embodiment, the second therapeutic agent is selected from one or more of emtricitabine, tenofovir disoproxil fumarate, ritonavir, lamivudine, zidovudine, tipranavir, enfuvirtide and ancriviroc.

In an even more specific embodiment, the patient is co-administered emtricitabine and tenofovir disoproxil fumarate.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formulas (I), (IA), (IB) or (IC) alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formulas (I), (IA), (IB) or (IC) for use in the treatment or prevention in a patient of a disease, disorder or symptom thereof delineated herein.

Diagnostic Methods and Kits

The compounds and compositions of this invention are also useful as reagents in methods for determining the concentration of vicriviroc in solution or biological sample such as plasma, examining the metabolism of vicriviroc and other analytical studies.

According to one embodiment, the invention provides a method of determining the concentration, in a solution or a biological sample, of vicriviroc, comprising the steps of:
a) adding a known concentration of a compound of Formulas (I), (IA), (IB) or (IC) to the solution of biological sample;
b) subjecting the solution or biological sample to a measuring device that distinguishes vicriviroc from a compound of Formulas (I), (IA), (IB) or (IC);
c) calibrating the measuring device to correlate the detected quantity of the compound of Formulas (I), (IA), (IB) or (IC) with the known concentration of the compound of Formulas (I), (IA), (IB) or (IC) added to the biological sample or solution; and
d) measuring the quantity of vicriviroc in the biological sample with said calibrated measuring device; and
e) determining the concentration of vicriviroc in the solution of sample using the correlation between detected quantity and concentration obtained for a compound of Formulas (I), (IA), (IB) or (IC).

Measuring devices that can distinguish vicriviroc from the corresponding compound of Formulas (I), (IA), (IB) or (IC) include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formulas (I), (IA), (IB) or (IC) comprising the steps of contacting the compound of Formulas (I), (IA), (IB) or (IC) with a metabolizing enzyme source for a period of time and comparing the amount of the compound of Formulas (I), (IA), (IB) or (IC) with the metabolic products of the compound of Formulas (I), (IA), (IB) or (IC) after the period of time.

In a related embodiment, the invention provides a method of evaluating the metabolic stability of a compound of Formulas (I), (IA), (IB) or (IC) in a patient following administration of the compound of Formulas (I), (IA), (IB) or (IC). This method comprises the steps of obtaining a serum, urine or feces sample from the patient at a period of time following the administration of the compound of Formulas (I), (IA), (IB) or (IC) to the subject; and comparing the amount of the compound of Formulas (I), (IA), (IB) or (IC) with the metabolic products of the compound of Formulas (I), (IA), (IB) or (IC) in the serum, urine or feces sample.

The present invention also provides kits for use to treat HIV infection. These kits comprise (a) a pharmaceutical composition comprising a compound of Formulas (I), (IA), (IB) or (IC) or a salt thereof, wherein said pharmaceutical composition is in a container; and (b) instructions describing a method of using the pharmaceutical composition to treat HIV infection.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of (S)-tert-Butyl 4-methyl-4-(3-methylpiperazin-1-yl)piperidine-1-carboxylate (26)

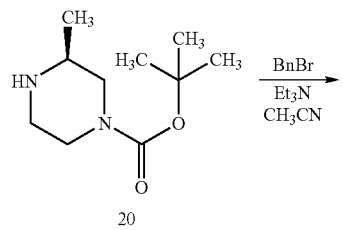

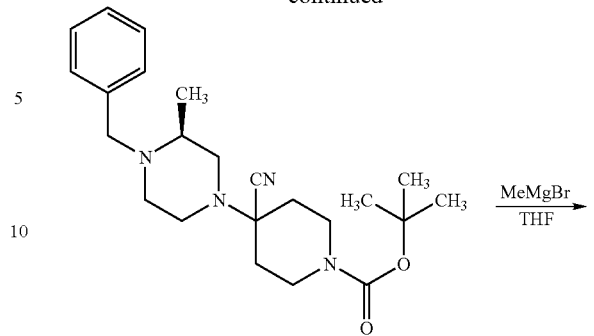

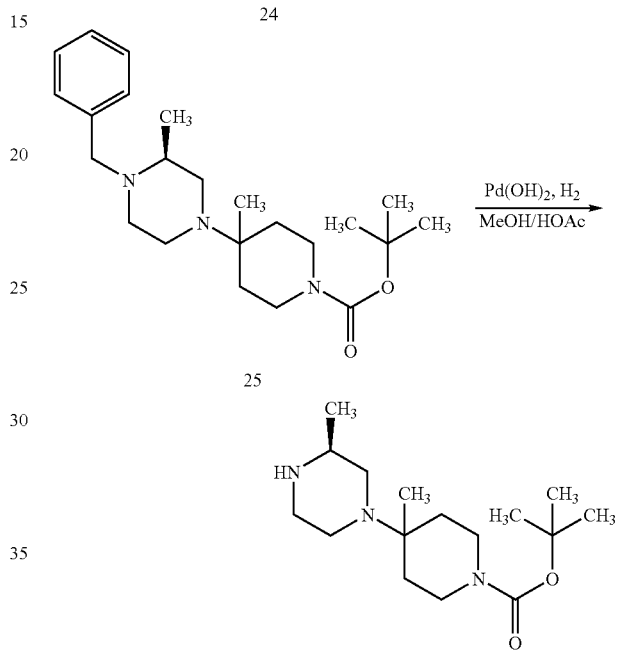

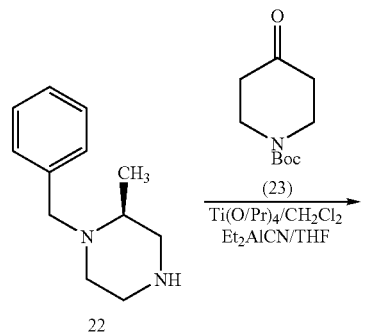

Step 1. (S)-tert-Butyl 4-benzyl-3-methylpiperazine-1-carboxylate (21). To a solution of commercially available (S)-tert-butyl 3-methylpiperazine-1-carboxylate (20)

(42.2 g, 210.7 mmol) in acetonitrile (200 mL) under nitrogen at 5° C. was added triethylamine (32.30 mL, 23.4 g, 231.7 mmol) followed by benzyl bromide (39.6 g, 231.8 mmol) dropwise over 20 minutes. The mixture was stirred at reflux overnight. After 18 hours the mixture was filtered to remove solids. The filtrate was concentrated under reduced pressure. The resultant oil was dissolved in dichloromethane (350 mL) and washed with 1N aqueous sodium hydroxide solution (2×100 mL). The organic solution was dried over sodium sulfate and concentrated under reduced pressure to give 47.5 g (78%) of 21 as an orange oil.

Step 2. (S)-1-Benzyl-2-methylpiperazine (22). To a stirred mixture of 21 (47.1 g, 162.2 mmol) in water (50 mL) under nitrogen at 10° C. was added an aqueous solution of 6 N HCl (100 mL) dropwise. Following addition of the acid, the mixture was allowed to warm to room temperature. After stirring for 20 hours, the mixture was cooled in an ice-bath and a 50% aqueous sodium hydroxide solution was added dropwise until the pH was approximately 10.5. The mixture was then extracted with dichloromethane (2×300 mL). The combined organic layers were dried over sodium sulfate and concentrated under reduced pressure. The resultant oil was distilled under reduced pressure to give 21.50 g (50%) of 22 as a yellow oil.

Step 3. (S)-tert-Butyl 4-(4-benzyl-3-methylpiperazin-1-yl)-4-cyanopiperidine-1-carboxylate (24). To a stirred solution of 22 (21.22 g, 111.52 mmol) in dichloromethane (65 mL) was added 1-Boc-4-piperidone (23) (22.22 g, 111.52 mmol) in one portion. Titanium tetraisopropoxide (45.75 mL, 44.38 g, 156.13 mmol) was added dropwise over 30 minutes while the mixture was agitated with a mechanical stirrer at room temperature. After 21 hours, tetrahydrofuran (115 mL) was added. A 1.0 M solution of diethylaluminum cyanide (117.10 mL, 117.10 mmol) was added dropwise over 20 minutes. The mixture was stirred at room temperature for 20 hours then cooled to 0° C. Ethyl acetate (113 mL) was added dropwise over 10 minutes. Celite (11 g) was added, followed by sodium bicarbonate (47 g) and saturated aqueous sodium sulfate solution (11 mL) over 20 minutes. Methanol (70 mL) was added and the mixture was filtered through Celite and concentrated under reduced pressure to give 36.94 g (83%) of 24 as a beige, waxy solid.

Step 4. (S)-tert-Butyl 4-(4-benzyl-3-methylpiperazin-1-yl)-4-methylpiperidine-1-carboxylate (25). To a stirred solution of 24 (36.90 g, 92.65 mmol) in THF (200 mL) at 0° C. under nitrogen was added a 3.0 M solution of methyl magnesium bromide in diethyl ether (92.65 mL, 277.96 mmol) over 30 minutes. The mixture was allowed to warm to room temperature overnight. After 21 hours the mixture was cooled to −5° C. Saturated aqueous ammonium chloride solution (500 mL) was added dropwise. [Note: a nitrogen stream was passed through the vessel into a trap with an outlet leading to a saturated aqueous sodium hydroxide solution to capture any hydrogen cyanide that may have been formed.] The mixture was allowed to warm to room temperature overnight following ammonium chloride addition with continued nitrogen flush. The mixture was then extracted with ethyl acetate (2×700 mL). The combined organic layers were washed with brine (300 mL), dried over sodium sulfate, and concentrated under reduced pressure to give 30.96 g (86%) of 25 as a viscous, yellow oil.

Step 5. (S)-tert-Butyl 4-methyl-4-(3-methylpiperazin-1-yl)piperidine-1-carboxylate (26). To a solution of 25 (30.87 g, 79.65 mmol) in methanol (250 mL) was added acetic acid (22.80 mL, 23.92 g, 398.26 mmol). The mixture was placed under nitrogen and 20 wt % palladium hydroxide on carbon (4 g) was added. The mixture was placed under a hydrogen atmosphere (55 psi) for 18 hours, then was filtered through Celite with a methanol rinse. The filtrate was concentrated under reduced pressure and the resultant oil was dissolved in dichloromethane (600 mL). The organic solution was washed with a 10% aqueous sodium hydroxide solution (500 mL) and the basic aqueous wash was extracted with dichloromethane (300 mL). The combined organic layers were washed with brine (400 mL), dried over sodium sulfate, and concentrated under reduced pressure to give 24.41 g (100%) of 26 as a light yellow oil.

Example 2

Synthesis of 4,6-Di(methyl-d$_3$)pyrimidine-5-(carboxylic acid-d$_1$) (5b)

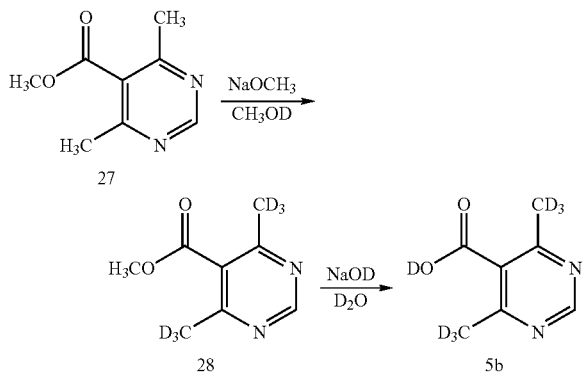

Scheme 6. Preparation of Intermediate 5b.

Step 1. Methyl 4,6-di(methyl-d$_3$)pyrimidine-5-carboxylate (28). Sodium metal (1.06 g, 45.76 mmol) was added to methanol-d (40 mL) [Cambridge Isotope, 99.8 atom % D] at room temperature and the mixture was stirred until the sodium metal fully dissolved. A solution of commercially available methyl 4,6-dimethylpyrimidine-5-carboxylate (27) (5.85 g, 35.20 mmol) in methanol-d (10 mL) was added and the mixture was stirred at reflux for 4 hours. The mixture was cooled to room temperature and concentrated under reduced pressure. Methanol-d (50 mL) was added to the resultant solid and the mixture was stirred at reflux for 72 hours. The mixture was cooled to room temperature and concentrated under reduced pressure. The resultant solid was dissolved in ethyl acetate (200 mL) and the organic solution was washed with saturated aqueous sodium bicarbonate solution (100 mL). The aqueous layer was extracted with ethyl acetate (100 mL). The combined organic layers were dried over sodium sulfate and concentrated under reduced pressure to give 3.78 g (65%) of 28 as a white, crystalline solid.

Step 2. 4,6-Di(methyl-d$_3$)pyrimidine-5-(carboxylic acid-d$_1$) (5b). To a suspension of 28 (3.69 g, 21.47 mmol) in deuterium oxide (20 mL) [Cambridge Isotope, 99.9 atom % D] was added a solution of 40% wt sodium deuteroxide in deuterium oxide (4.40 mL, 1.76 g, 42.95 mmol) [Acros, 99+ atom % D]. The mixture was stirred at 55° C. under nitrogen for 3.5 hours, then was cooled to room temperature. A 35% wt solution of DCl in deuterium oxide [Aldrich, 99 atom % D] was added dropwise until the pH was approximately 2. The resultant suspension was filtered and rinsed with cold deuterium oxide. The collected solid was dried under vacuum at room temperature for 4 hours to give 1.62 g (49%) of 5b as a beige solid. ¹H NMR analysis indicated <1% hydrogen present at the methyl groups.

Example 3

Synthesis of (4,6-Di(methyl-d₃)pyrimidin-5-yl)(4-((S)-4-((R)-2-(methoxy-d₃)-1-(4-(trifluoromethyl)phenyl)ethyl)-3-methylpiperazin-1-yl)-4-methylpiperidin-1-yl)methanone (Compound 107)

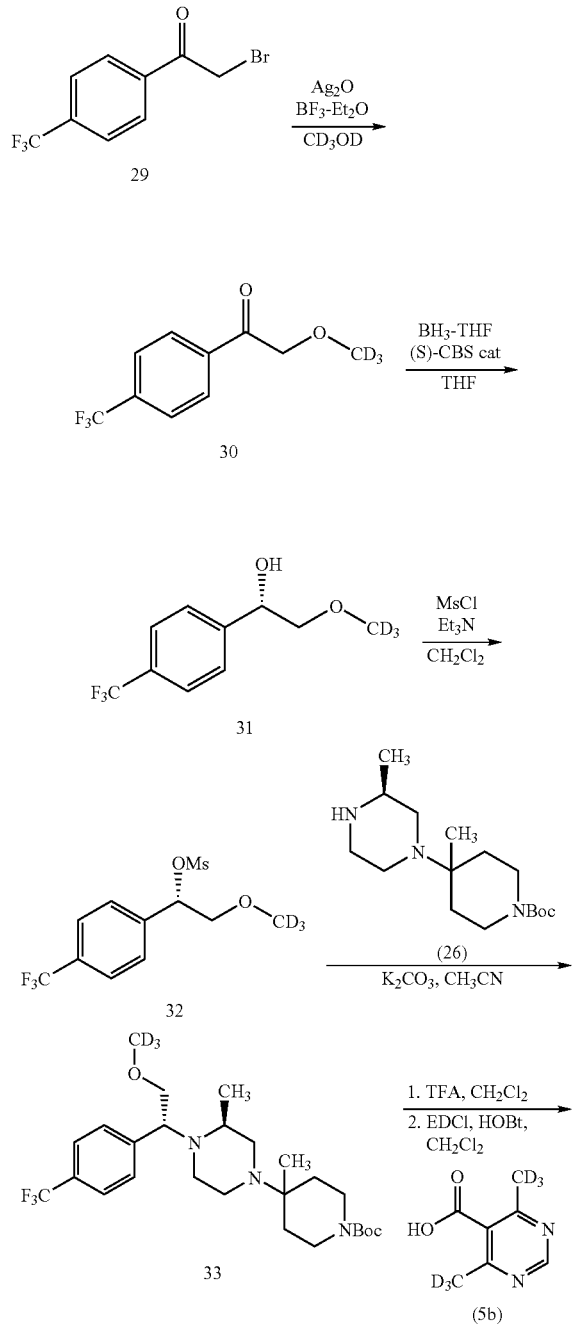

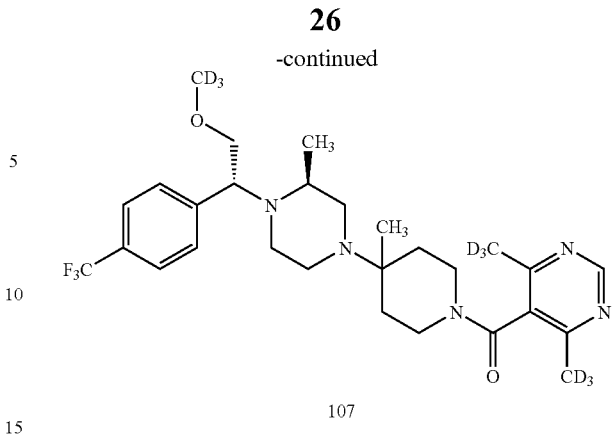

Step 1. 2-(Methoxy-d₃)-1-(4-(trifluoromethyl)phenyl)ethanone (30). To a stirred solution of boron trifluoride etherate (171 mL) and methanol-d₄ (55 mL) [Cambridge Isotope, 99 atom % D] under nitrogen at 0° C. was added silver (I) oxide (42.35 g, 182.74 mmol) in one portion. The mixture was allowed to stir until all solids had dissolved, then was warmed to room temperature. Commercially available 2-bromo-1-(4-(trifluoromethyl)phenyl)ethanone (29) (24.40 g, 91.37 mmol) in methanol-d₄ (50 mL) was added and the mixture was allowed to stir at room temperature for 3.5 days. The mixture was filtered to remove the solids. The filtrate was poured into MTBE (500 mL) and washed with water (300 mL). The organic layer was dried over sodium sulfate and concentrated under reduced pressure. The resultant oil was purified by silica gel chromatography using an Analogix automated chromatography system eluting with 0-100% ethyl acetate in heptanes to give 12.3 g (61%) of 30 as a white solid.

Step 2. (S)-2-(Methoxy-d₃)-1-(4-(trifluoromethyl)phenyl)ethanol (31). To a stirred solution of 30 (4.45 g, 20.12 mmol) under nitrogen in anhydrous THF (78 mL) at room temperature was added (S)-CBS catalyst (0.56 g, 2.01 mmol). After the (S)-CBS catalyst had dissolved, a 1.0 M solution of BH₃ in THF (12.07 mL, 12.07 mmol) was added dropwise over 20 minutes. The mixture was allowed to stir at room temperature for 19 hours, then a solution of sodium hydroxide (2.41 g, 60.35 mmol) in water (60 mL) was added. The resulting mixture was stirred at room temperature for 30 minutes, then a solution of 30% hydrogen peroxide (2.05 g, 60.35 mmol) in water (30 mL) was added and the resulting mixture was allowed to stir for 30 minutes. The mixture was then poured into ethyl acetate (200 mL). Following extraction, the organic layer was washed with brine (75 mL), dried over sodium sulfate, and concentrated under reduced pressure to afford a yellow oil. The resultant oil was purified via silica gel chromatography using an Analogix automated chromatography system eluting with 0-80% ethyl acetate in heptanes to give 3.69 g (78%) of 31 as a clear, light yellow oil. Chiral HPLC analysis [Chiral OD, 250 mm×4.6 mm, 10 μm. Isocratic 5% isopropanol/hexane at 0.800 mL/min] indicates an ee of 61.4% for the isolated product (31).

Step 3. (S)-2-(Methoxy-d₃)-1-(4-(trifluoromethyl)phenyl)ethyl methanesulfonate (32). To a stirred solution of 31 (3.70 g, 16.58 mmol) in anhydrous dichloromethane (50 mL) at 0° C. was added triethylamine (2.77 mL, 2.01 g, 19.89 mmol). Methanesulfonyl chloride (0.96 mL, 1.42 g, 12.43 mmol) was added dropwise to the mixture over 5 minutes. The mixture was allowed to stir at 0° C. for 16 hours. The solvent was removed under reduced pressure. The resultant oil was dissolved in MTBE (200 mL) and washed with brine (100 mL).

The organic layer was separated, dried over sodium sulfate, and concentrated under reduced pressure to give 4.85 g (97%) of 32 as an orange oil.

Step 4. tert-Butyl 4-((S)-4-((R)-2-(methoxy-d$_3$)-1-(4-(trifluoromethyl)phenyl)ethyl)-3-methylpiperazin-1-yl)-4-methylpiperidine-1-carboxylate (33). To a stirred solution of 32 (4.80 g, 15.93 mmol) in anhydrous acetonitrile (60 mL) was added 26 (4.74 g, 15.93 mmol, see Example 1) and potassium carbonate (2.64 g, 19.12 mmol). The mixture was heated to reflux and allowed to stir for approximately 5.5 days. The mixture was cooled to room temperature and poured into saturated aqueous sodium bicarbonate (120 mL). This mixture was extracted with ethyl acetate (350 mL). The organic layer was washed with brine (100 mL), dried over sodium sulfate, and concentrated under reduced pressure. The resultant oil was purified via silica gel chromatography using an Analogix automated chromatography system eluting with 0-100% ethyl acetate in heptanes to give 4.50 g (56%) of 33 as a yellow oil. [Note: the desired diastereomer, 33, eluted faster and could be easily distinguished from the minor diastereomer by HPLC analysis of the fractions. HPLC analysis did not detect any of the minor diastereomer in the collected fractions containing 33.]

Step 5. (4,6-Di(methyl-d$_3$)pyrimidin-5-yl)(4-((S)-4-((R)-2-(methoxy-d$_3$)-1-(4-(trifluoromethyl)phenyl)ethyl)-3-methylpiperazin-1-yl)-4-methylpiperidin-1-yl)methanone (Compound 107). To a stirred solution of 33 (4.46 g, 8.87 mmol) in dichloromethane (30 mL) at 0° C. was added trifluoroacetic acid (6.0 mL). The mixture was allowed to warm to room temperature and stirring was continued for 18 hours. The resulting mixture was poured into saturated aqueous sodium bicarbonate solution (150 mL), the dichloromethane layer was separated and the remaining aqueous layer was extracted with ethyl acetate (150 mL). The combined organic layers were washed with aqueous 1N HCl (250 mL). The acidic layer was brought to a pH of approximately 10 using 24% aqueous sodium hydroxide. The basic mixture was extracted with ethyl acetate (2×200 mL). The organic solution was dried over sodium sulfate and concentrated under reduced pressure to give 2.98 g (83%) of the deprotected intermediate (33-desBoc, not shown) as a yellow oil.

To a stirred solution of 5b (0.45 g, 2.87 mmol, see Example 2) in dichloromethane (5.0 mL) was added hydroxybenzotriazole (0.30 g, 2.21 mmol) followed by 1-ethyl-3-(3-dimethylaminopropyl) carbodiimide (0.51 g, 2.65 mmol). The mixture was allowed to stir at room temperature for 30 minutes. To this mixture was added a solution of 33-desBoc (0.89 g, 2.21 mmol) in dichloromethane (5.0 mL). After stirring at room temperature for 44 hours, the mixture was concentrated under reduced pressure. The resultant oil was dissolved in ethyl acetate (120 mL) and the organic solution was extracted with 1N HCl$_{(aq)}$ (2×150 mL). The combined acidic aqueous layers were made basic using 24% aqueous sodium hydroxide until the pH was approximately 10. This basic mixture was then extracted with dichloromethane (2×200 mL). The combined organic layers were dried over sodium sulfate and concentrated under vacuum. The resultant oil was purified via silica gel chromatography using an Analogix automated chromatography system eluting with 0-5% methanol in dichloromethane to yield a clear, colorless oil. The oil was dissolved in acetonitrile (5 mL) and treated with 2 mL of deuterium oxide. Upon concentration under reduced pressure a white amorphous solid formed. The solid was dried at 50° C. in a vacuum oven for 16 hours to give 754 mg (63%) of Compound 107 as a powdery white solid. $^1$H-NMR (300 MHz, CDCl$_3$): δ 0.93 (s, 3H), 1.18 (d, J=6.1, 3H), 1.22-1.30 (m, 1H), 1.37-1.46 (m, 1H), 1.72-1.84 (m, 1H), 1.92-2.05 (m, 1H), 2.23-2.40 (m, 3H), 2.44-2.51 (m, 2H), 2.58-2.68 (m, 1H), 2.95-3.00 (m, 1H), 3.05-3.20 (m, 1H), 3.35-3.49 (m, 2H), 3.69-3.80 (m, 2H), 3.99-4.07 (m, 1H), 4.21-4.25 (m, 1H), 7.55 (d, J=2.6, 4H), 8.94 (s, 1H). $^{13}$C-NMR (75 MHz, CDCl$_3$): δ 17.97, 18.01, 35.18, 35.26, 36.08, 36.17, 36.98, 37.05, 42.03, 42.12, 45.22, 45.75, 52.17, 53.28, 71.49, 124.97, 125.02, 128.56, 129.58, 146.06, 157.48, 162.48, 165.90. HPLC (method: Waters Atlantis T3 2.1×50 mm 3 μm C18-RP column-gradient method 5-95% ACN+0.1% formic acid in 14 min (1.0 mL/min) with 4 min hold at 95% ACN; Wavelength: 254 nm): retention time: 4.72 min; 98.3% purity. Chiral HPLC (method: 250 mm×4.6 mm Chiral OD column-isocratic method 95% hexane/5% isopropanol for 40 min (1.0 mL/min); Wavelength: 210 nm): retention time: 13.56 min (50.6%); 18.20 min (48.7%). MS (M+H): 543.3. Elemental Analysis (C$_{28}$H$_{29}$D$_9$F$_3$N$_5$O$_2$): Calculated: C=61.98, H=7.06, N=12.91, F=10.50. Found: C=61.76, H=7.08, N=12.84, F=10.76.

Example 4

Synthesis of (4,6-Di(methyl-d$_3$)pyrimidin-5-yl)(4-((S)-4-((R)-2-(methoxy-d$_3$)-1-(4-(trifluoromethyl)phenyl)-2,2-d$_2$-ethyl)-3-methylpiperazin-1-yl)-4-methylpiperidin-1-yl)methanone (Compound 105)

Intermediate 30-d$_5$ was prepared as shown in Scheme 8 below. Compound 105 was prepared from 30-d$_5$ as generally outlined in Scheme 7 above.

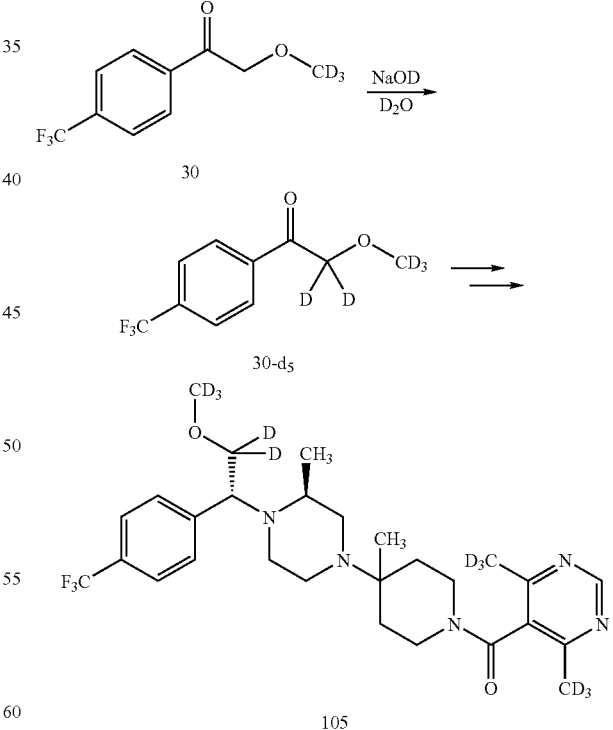

Step 1. 2-(Methoxy-d$_3$)-1-(4-(trifluoromethyl)phenyl)ethan-d$_2$-one (30-d$_5$). To a stirred solution of 30 (3.0 g, 13.6 mmol) in deuterium oxide (30 mL) [Cambridge Isotope, 99.9 atom % D] was added 40% wt sodium deuteroxide in deuterium oxide (0.4 mL) [Acros, 99+ atom % D]. To this mixture was added methanol-d [Cambridge Isotope, 99.8 atom % D] (approximately 10 mL) to aid salvation. The yellow-orange solution was allowed to stir for 2 hours at room temperature. To this mixture was added 35% DCl in deuterium oxide [Aldrich, 99 atom % D] until the pH was approximately 5. The mixture was extracted with ethyl acetate (2×100 mL). The organic layer was separated, dried over sodium sulfate, and concentrated under reduced pressure to afford a yellow oil. The resultant oil was purified via silica gel chromatography using an Analogix automated chromatography system eluting with 0-80% ethyl acetate in heptanes to give 2.06 g (69%) of 30-$d_5$ as a yellow, crystalline solid.

Step 2. (S)-2-(Methoxy-$d_3$)-1-(4-(trifluoromethyl)phenyl)-2,2-$d_2$-ethanol (31-$d_5$). To a stirred solution of 30-$d_5$ (2.00 g, 8.96 mmol) under nitrogen in anhydrous THF (36 mL) at room temperature was added (S)-CBS catalyst (0.25 g, 0.90 mmol). After the (S)-CBS catalyst had dissolved, a 1.0 M solution of $BH_3$ in THF (5.38 mL, 5.38 mmol) was added dropwise over 20 minutes. The mixture was allowed to stir at room temperature for 15 hours, then a solution of sodium hydroxide (1.08 g, 26.88 mmol) in water (15 mL) was added. The resulting mixture was stirred at room temperature for 30 minutes, then a solution of 30% hydrogen peroxide (0.91 g, 26.88 mmol) in water (15 mL) was added. The mixture was stirred for 30 minutes, then was then poured into ethyl acetate (150 mL). Following extraction, the organic layer was washed with brine (75 mL), dried over sodium sulfate, and concentrated under reduced pressure to afford a yellow oil. The resultant oil was purified via silica gel chromatography using an Analogix automated chromatography system eluting with 0-80% ethyl acetate in heptanes to give 1.37 g (68%) of 31-$d_5$ as a clear, light yellow oil. Chiral HPLC analysis [Chiral OD, 250 mm×4.6 mm, 10 μm. Isocratic 5% isopropanol/hexane at 0.800 mL/min] indicates an ee of 68.2% for the isolated product (31-$d_5$).

Step 3. (S)-2-(Methoxy-$d_3$)-1-(4-(trifluoromethyl)phenyl)-2,2-$d_2$-ethyl methanesulfonate (32-$d_5$). To a stirred solution of 31-$d_5$ (2.53 g, 11.23 mmol) in anhydrous dichloromethane (30 mL) at 0° C. was added triethylamine (3.13 mL, 2.27 g, 22.46 mmol). Methanesulfonyl chloride (1.04 mL, 1.54 g, 13.48 mmol) was added dropwise over 5 minutes and the mixture was allowed to stir at 0° C. for 3 hours. The solvent was removed under reduced pressure. The resultant oil was dissolved in MTBE (200 mL) and the organic solution was washed with brine (100 mL). The organic layer was separated, dried over sodium sulfate, and concentrated under reduced pressure to give 3.45 g (100%) of 32-$d_5$ as a yellow oil.

Step 4. tert-Butyl 4-((S)-4-((R)-2-(methoxy-$d_3$)-1-(4-(trifluoromethyl)phenyl)-2,2-$d_2$-ethyl)-3-methylpiperazin-1-yl)-4-methylpiperidine-1-carboxylate (33-$d_5$). To a stirred solution of 32-$d_5$ (3.38 g, 11.14 mmol) in anhydrous acetonitrile (35 mL) was added 26 (3.31 g, 11.14 mmol, see Example 1) and potassium carbonate (1.85 g, 13.37 mmol). The mixture was stirred at reflux for approximately 4.5 days, then was cooled to room temperature and poured into saturated aqueous sodium bicarbonate (150 mL). The resulting mixture was extracted with ethyl acetate (2×200 mL) and the combined organic layers were washed with brine (100 mL), dried over sodium sulfate, and concentrated under reduced pressure. The resultant oil was purified via silica gel chromatography using an Analogix automated chromatography system eluting with 0-100% ethyl acetate in heptanes to give 2.40 g (43%) of 33-$d_5$ as a yellow oil. [Note: the desired diastereomer, 33-$d_5$, eluted faster and could be easily distinguished from the minor diastereomer by HPLC analysis of the fractions. HPLC analysis did not detect any of the minor diastereomer in the collected fractions containing 33-$d_5$]

Step 5. (4,6-Di(methyl-$d_3$)pyrimidin-5-yl)(4-((S)-4-((R)-2-(methoxy-$d_3$)-1-(4-(trifluoromethyl)phenyl)-2,2-$d_2$-ethyl)-3-methylpiperazin-1-yl)-4-methylpiperidin-1-yl) methanone (Compound 105). To a stirred solution of 33-$d_5$ (2.36 g, 4.68 mmol) in dichloromethane (40 mL) at 0° C. was added trifluoroacetic acid (6.0 mL). The mixture was allowed to warm to room temperature, was stirred for 16 hours, then was poured into aqueous 1N HCl (100 mL). The mixture was extracted with ethyl acetate (2×). The combined acidic layers were brought to a pH of approximately 10 using 24% aqueous sodium hydroxide. The basic mixture was extracted with ethyl acetate (2×150 mL). The combined organic layers were dried over sodium sulfate and concentrated under reduced pressure to give 1.78 g (94%) of the deprotected intermediate (33-$d_5$-desBoc, not shown) as a foamy, off-white solid.

To a stirred solution of 5b (0.58 g, 3.66 mmol, see Example 2) in dichloromethane (5.0 mL) was added hydroxybenzotriazole (0.38 g, 2.82 mmol) followed by 1-ethyl-3-(3-dimethylaminopropyl) carbodiimide (0.65 g, 3.38 mmol). The mixture was allowed to stir at room temperature for 30 minutes. To this mixture was added a solution of 33-$d_5$-desBoc (1.14 g, 2.82 mmol) in dichloromethane (5.0 mL). After stirring at room temperature for 72 hours, the mixture was concentrated under reduced pressure and the resultant oil was dissolved in ethyl acetate (120 mL). The organic solution was extracted with 1N $HCl_{(aq)}$ (2×125 mL). The combined acidic aqueous layers were made basic using 24% aqueous sodium hydroxide until the pH was approximately 10. This basic mixture was then extracted with dichloromethane (2×200 mL). The combined organic layers were dried over sodium sulfate and concentrated under reduced pressure. The resultant oil was purified via silica gel chromatography using an Analogix automated chromatography system eluting with 0-5% methanol in dichloromethane to give a clear, light yellow oil. The oil was dissolved in acetonitrile (5 mL) and treated with 2 mL of deuterium oxide. Upon concentration under reduced pressure a white solid formed. The solid was dried at 50° C. in a vacuum oven for 16 hours to give 535 mg (35%) of Compound 105 as a powdery white solid. $^1$H-NMR (300 MHz, $CDCl_3$): δ 0.93 (s, 3H), 1.19 (d, J=6.1, 3H), 1.22-1.31 (m, 1H), 1.38-1.46 (m, 1H), 1.75-1.84 (m, 1H), 1.95-2.03 (m, 1H), 2.23-2.40 (m, 3H), 2.44-2.51 (m, 2H), 2.58-2.70 (m, 1H), 2.95-3.01 (m, 1H), 3.05-3.18 (m, 1H), 3.35-3.49 (m, 2H), 4.01-4.03 (m, 1H), 4.21-4.27 (m, 1H), 7.55 (d, J=3.2, 4H), 8.95 (s, 1H). $^{13}$C-NMR (75 MHz, $CDCl_3$): δ 17.97, 18.01, 35.18, 35.26, 36.08, 36.17, 36.97, 37.04, 42.02, 42.11, 45.21, 45.78, 52.14, 53.28, 124.97, 125.02, 128.56, 129.70, 146.03, 157.48, 162.46, 165.89. HPLC (method: 20 mm C18-RP column-gradient method 2-95% ACN+0.1% formic acid in 3.3 min with 1.7 min hold at 95% ACN; Wavelength: 254 nm): retention time: 2.62 min; 99.6% purity. Chiral HPLC (method: 250 mm×4.6 mm Chiral OD column-isocratic method 95% hexane/5% isopropanol for 40 min (0.80 mL/min); Wavelength: 220 nm): retention time: 21.52 min (50.4%); 27.72 min (49.6%). MS (M+H): 545.4. Elemental Analysis ($C_{28}H_{27}D_{11}F_3N_5O_2$): Calculated: C=61.75, H=7.03, N=12.86, F=10.46. Found: C=61.59, H=7.13, N=12.84, F=10.43.

Example 5

Evaluation of Metabolic Stability in Human Liver Microsomes

Materials: Human liver microsomes (20 mg/mL) were obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) were purchased from Sigma-Aldrich.

Stock solutions (7.5 mM) of Compound 105, Compound 107 and vicriviroc were prepared in DMSO. The 7.5 mM stock solutions were diluted to 12.5 µM in acetonitrile (ACN). The 20 mg/mL human liver microsomes were diluted to 0.625 mg/mL in 0.1 M potassium phosphate buffer, pH 7.4, containing 3 mM $MgCl_2$. The diluted microsomes were added to wells of a 96-well deep-well polypropylene plate in triplicate. A 10 µL aliquot of the 12.5 µM test compound was added to the microsomes and the mixture was pre-warmed for 10 minutes. Reactions were initiated by addition of pre-warmed NADPH solution. The final reaction volume was 0.5 mL and contained 0.5 mg/mL human liver microsomes, 0.25 µM test compound, and 2 mM NADPH in 0.1 M potassium phosphate buffer, pH 7.4, and 3 mM $MgCl_2$. The reaction mixtures were incubated at 37° C., and 50 µL aliquots were removed at 0, 5, 10, 20, and 30 minutes and added to shallow-well 96-well plates which contained 50 µL of ice-cold ACN with internal standard to stop the reactions. The plates were stored at 4° C. for 20 minutes after which 100 µL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer. 7-Ethoxycoumarin (1 µM) was used as a positive control. The experiment was repeated a second time to confirm the results.

Data analysis: The in vitro $t_{1/2}$s for test compounds were calculated from the slopes of the linear regression of % parent remaining (ln) vs incubation time relationship using the following formula: in vitro $t_{1/2}$=0.693/k, where k=–[slope of linear regression of % parent remaining(ln) vs incubation time]. Data analysis was performed using Microsoft Excel Software.

The results are shown in the FIGURE and Table 1, below.

TABLE 1

Calculated Half-Lives of Compounds of the Invention in Human Liver Microsomes.

| | $t_{1/2}$ (minutes) | | | |
|---|---|---|---|---|
| Compound | Experiment 1 | Experiment 2 | Ave $t_{1/2}$ (minutes) | % Difference* |
| Vicriviroc | 56 | 54 | 55 | — |
| Compound 105 | 105 | 90 | 98 | 78 |
| Compound 107 | 65 | 67 | 66 | 20 |

*% Difference = [(deuterated species) – (nondeuterated species)](100)/(nondeuterated species)

Under the assay conditions tested, the in vitro $t_{1/2}$s of Compound 105 and 107 showed ~77% and 20% increase, respectively, over nondeuterated vicriviroc.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A compound selected from any one of the compounds set forth below:

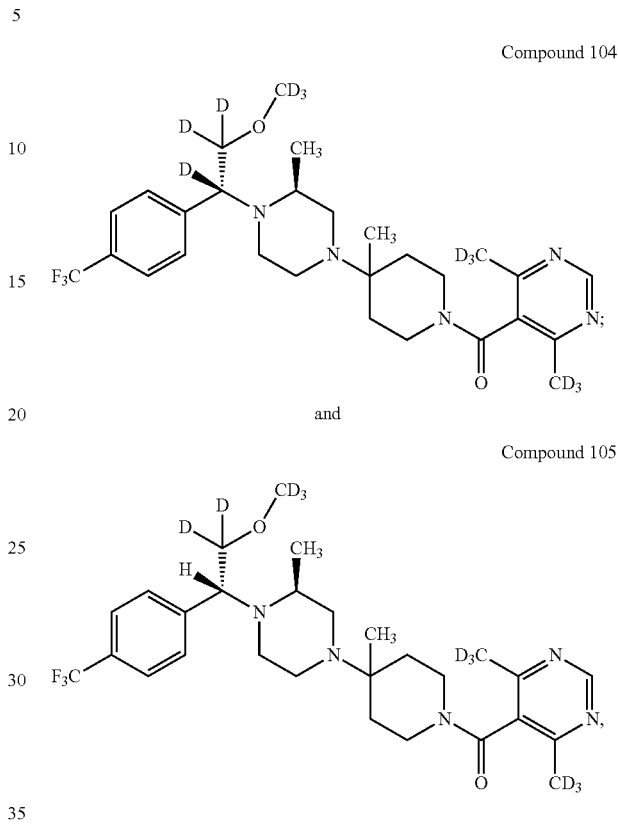

or a pharmaceutically acceptable salt of any of the foregoing.

2. A pyrogen-free pharmaceutical administration comprising a compound of claim 1 or a pharmaceutically acceptable salt thereof; and a pharmaceutically acceptable carrier.

3. The composition of claim 2 comprising a second therapeutic agent selected from an HIV protease inhibitor, a NNRTI, a NRTI, a second viral entry inhibitor, an integrase inhibitor, an immune based antiretroviral agent, a viral maturation inhibitor, or a combination of two or more of the foregoing.

4. The composition of claim 3, wherein the second therapeutic agent is selected from emtricitabine, tenofovir disoproxil fumarate, ritonavir, lamivudine, zidovudine, tipranavir, enfuvirtide and ancriviroc.

5. The composition of claim 4, wherein the second therapeutic agent is selected from ritonavir, lamivudine, emtricitabine, tenofovir disoproxil fumarate, and zidovudine.

6. A method of treating an HIV—1 infection in a patient comprising the step of administering to the patient an effective amount of a compound of claim 1 or a pharmaceutically acceptable salt thereof.

7. The method of claim 6 comprising the additional step of co-administering to the patient in need thereof a second therapeutic agent selected from one or more of an HIV protease inhibitor, a NNRTI, a NRTI, a second viral entry inhibitor, an integrase inhibitor, an immune based antiretroviral agent, and a viral maturation inhibitor.

8. The method of claim 7, wherein the second therapeutic agent is selected from one or more of emtricitabine, tenofovir disoproxil fumarate, ritonavir, lamivudine, zidovudine, tipranavir, enfuvirtide and ancriviroc.

9. The method of claim 8, wherein the second therapeutic agent is selected from emtricitabine and tenofovir disoproxil fumarate.

10. A compound of claim 1, wherein any atom not designated as deuterium is present at its natural isotopic abundance.

* * * * *